United States Patent [19]
Vosganiantz

[11] 3,945,950
[45] Mar. 23, 1976

[54] SOLID PERFUMED COMPOSITIONS OF MATTER

[75] Inventor: Jean-Jacques Vosganiantz, Amboise, France

[73] Assignee: Universal Oil Products Company, Des Plaines, Ill.

[22] Filed: Oct. 2, 1974

[21] Appl. No.: 511,157

[52] U.S. Cl. .................... 252/522; 239/53; 239/60
[51] Int. Cl.² .......................................... C11B 9/00
[58] Field of Search ............ 252/522; 239/6, 34, 53, 239/60

[56] References Cited
UNITED STATES PATENTS

| | | | |
|---|---|---|---|
| 3,261,746 | 7/1966 | Copley | 252/522 |
| 3,310,472 | 3/1967 | Kohl | 252/522 |
| 3,767,787 | 10/1973 | Segal | 252/522 |

*Primary Examiner*—C. Davis
*Attorney, Agent, or Firm*—James R. Hoatson, Jr.; Raymond H. Nelson; William H. Page II

[57] ABSTRACT

Solid compositions of matter containing perfumery composites will also contain a mono($C_1$ to $C_4$ alkyl) ether of diethylene glycol whereby the evaporation of the perfumery composite may be regulated to a constant value.

9 Claims, No Drawings

SOLID PERFUMED COMPOSITIONS OF MATTER

This invention relates to solid support blocks which contain an aromatic or perfumery composite. More specifically, the invention is concerned with the inclusion of certain compounds of the type hereinafter set forth whereby the evaporation of the composite which provides a pleasant odor may be controlled and regulated.

Solid support blocks for aromatic or pleasant smelling composites have, in the past, been found to be erratic in the evaporation of the olfactory components of the block. As will hereinafter be shown in greater detail, it has now been discovered that, by including certain compounds, it is possible to regulate the evaporation of the olfactory component of the composition of matter whereby said evaporation will occur at a controlled and regular rate.

It is therefore an object of this invention to provide a novel support block for perfumery composites.

A further object of this invention is to provide a support block for perfumery composites, said support block containing certain compounds whereby the evaporation of the olfactory portion of the block is controlled.

In one aspect an embodiment of this invention resides in a solid perfumed composition of matter comprising a mixture of a gelling agent, inert liquids, an aromatic composite and a mono($C_1$ to $C_4$ alkyl) ether of diethylene glycol.

A specific embodiment of this invention is found in a solid perfumed composition of matter comprising a mixture of from about 2% to about 10% by weight of a gelling agent, from about 2% to about 40% by weight of an aromatic composite, from about 10% to about 20% by weight of inert liquids, and from about 45% to about 86% by weight of a mono($C_1$ to $C_4$ alkyl) ether of diethylene glycol.

Other objects and embodiments will be found in the following further detailed description of the present invention.

As hereinbefore set forth, it has now been discovered that, by adding a monoalkyl ether of diethylene glycol, and preferably a monoalkyl ether of diethylene glycol in which the alkyl portion of the ether contains from 1 to 4 carbon atoms, said ether being referred to as a mono($C_1$ to $C_4$ alkyl) ether of diethylene glycol, to a support block for a perfumery composite, it is possible to regulate the evaporation of the perfumery or olfactory composite. The support blocks containing a pleasant smelling composite are utilized for air fresheners, some examples of these air fresheners being sold under the tradenames Air-wick, Freshness, Fresh Hours, etc. During the use of these solid perfumery composites as air fresheners, the perfumery composite present in the final composition of matter will, due to the volatility thereof, evaporate. However, the evaporation of the aromatic compounds or materials has, in the past, been erratic and not regular in nature, the weight loss of the blocks tending to be greater when first used and then tending to flatten out upon further use thereof. However, by utilizing the compounds of the present invention, it is possible to regulate the evaporation of the aromatic materials in the solid composition of matter at such a rate so that the effective perfumery composite will be present in a much longer period of time. This is due in part to the fact that the mono($C_1$ to $C_4$ alkyl) ethers of diethylene glycol which are utilized possess a volatility which is similar in nature to that of the aromatic materials which are used to impart the pleasant fragrances in the perfumery composite.

Heretofore, the support blocks which were utilized in commerce were compounded by admixing a gelling agent and a mixture of inert liquids along with the perfumery composite. The inert liquids which have been used in commercial support blocks usually consisted of water, alcohols such as methyl alcohol, ethyl alcohol, n-propyl alcohol, etc.; glycols such as methylene glycol, ethylene glycol, propylene glycol or derivatives thereof. However, as hereinbefore set forth, either the volatility of the organic liquids differed from the volatility of the aromatic materials present in the perfumery composite and therefore contributed to the uneven evaporation of the aforesaid aromatic materials, such is the case for water and low molecular weight alkanols, or the organic liquids were hygroscopic and poor solvents for perfumery composites, specific examples of these organic liquids being ethylene glycol, propylene glycol, etc. In contradistinction to this, it has now been discovered that, by utilizing a mono($C_1$ to $C_4$ alkyl) ether of diethylene glycol in an amount so that said ether is present as a major portion of the composite, it is possible to obtain support blocks containing perfumery composites which permit the evaporation of the aromatic materials in a regular fashion.

The solid perfumed compositions of matter of the present invention will, therefore, comprise a mixture of a gelling agent such as, for example, a fatty acid soap containing from 10 to about 22 carbon atoms in length, said soaps including the alkali metal salts such as the sodium, potassium, lithium, etc., salts of capric acid, undecylic acid, lauric acid, tridecoic acid, myristic acid, pentadecanoic acid, palmitic acid, margaric acid, stearic acid, nondecylic acid, arachidic acid, behenic acid, etc., said gelling agent being present in an amount in the range of from about 2% to about 10% by weight of the finished composition of matter; an inert liquid or mixture of inert liquids including water, ethylene glycol, propylene glycol, butylene glycol, etc., said inert liquids being present in the range of from about 10% to about 20% by weight of the finished composition of matter; an aromatic composite consisting of a mixture of aromatic materials which may be present in any proportion necessary to give said composite a pleasant fragrance, said aromatic materials including alcohols, aldehydes, ketones, etc., said aromatic composite being present in an amount in the range of from about 2% to about 40% by weight of the finished composition of matter; and a mono($C_1$ to $C_4$ alkyl) ether of diethylene glycol such as the monomethyl ether of diethylene glycol, the monoethyl ether of diethylene glycol, the monopropyl ether of diethylene glycol, the monobutyl ether of diethylene glycol, etc., said mono($C_1$ to $C_4$ alkyl) ether of diethylene glycol being present in an amount in the range of from about 45% to about 86% by weight of the finished composition of matter. It is to be noted from the above proportions of compounds that the mono($C_1$ to $C_4$ alkyl) ethers of diethylene glycol are present in a major amount, that is over 50% of all of the volatile components which are present in the mixture. It is to be understood that the aforementioned mono($C_1$ to $C_4$ alkyl) ethers of diethylene glycols are only given as representative examples and that the present invention is not necessarily limited thereto.

The solid perfumed composition of matter may be prepared in any suitable manner. For example, one method of preparing the desired composition of matter is to admix the fatty acid with the mono($C_1$ to $C_4$ alkyl) ether of diethylene glycol. After the fatty acid, such as stearic acid, has dissolved in the mono($C_1$ to $C_4$ alkyl) ether of diethylene glycol, such as the monoethyl ether of diethylene glycol, the inert liquids comprising, for example, an aqueous solution of an alkali metal hydroxide, and, if so desired, ethylene glycol, are then admixed with the previously prepared mixture, said admixing being effected at an elevated temperature in the range of from about 70° to about 80° C. By this method, the gelling agent (an alkali metal salt of a fatty acid) is prepared in situ. It is also contemplated within the scope of this invention that the gelling agent comprising the alkali metal salt of a fatty acid can be prepared prior to addition to the inert liquids and thereafter dissolved therein. After thoroughly admixing the inert liquids, the fatty acid and the mono($C_1$ to $C_4$ alkyl) ether of diethylene glycol for a period of from about 10 seconds to about 1 minute, the aromatic composite is added, the mixture is then agitated for an additional period of 10 seconds to 1 minute and the composition of matter is then placed in a desired mold. The composition of matter is allowed to cool to room temperature whereby it forms a solid, following which it is removed and utilized for the purpose hereinbefore set forth in greater detail.

The perfumery composites which will form one component of the solid perfumed composition of matter of the present invention may, as hereinbefore set forth, comprise a mixture of various organic compounds, either naturally occurring or synthetic, comprising alcohols, aldehydes, ketones, esters, etc., the specific combination of these compounds resulting in a composite which may be utilized in the present invention would possess the following recipe:

| Ingredient | Parts by Weight |
| --- | --- |
| N-octanal | 0.5 |
| Capraldehyde | 0.5 |
| Resin benzoin | 3.0 |
| Resin labdanum | 1.5 |
| Lavandin | 15.5 |
| Polyalkylated acetyl tetralin | 1.5 |
| Neroyl | 15.0 |
| Citral diethyl acetate | 30.0 |
| Orange sweet | 5.0 |
| Rosemary | 3.0 |

Likewise, another example of a perfumery composite which may be used and which will possess a fragrance of rose will comprise the following ingredients or components:

| Ingredient | Parts by Weight |
| --- | --- |
| Citronellol | 45 |
| Citronellyl acetate | 6 |
| Benzophenone | 5 |
| Nerol | 10 |
| Linalool | 5 |
| Hydroxycitronellal | 10 |
| Phenylethyl alcohol | 3 |
| Phenylethyl dimethyl acrylate | 3 |
| Oil bois de rose | 8 |
| Isoeugenol | 0.5 |
| Oil caraway | 0.5 |
| n-Decanal | 0.5 |
| Isomenthol | 1.5 |

It is to be understood that these composites are given merely for the purposes of illustration and that any other composite which possesses a pleasant fragrance such as those of flowers, herbs, etc., may be used as one of the components of the final composition of matter of the present invention.

The following examples are given to illustrate the novel solid compositions of matter of the present invention and the ability of these compositions of matter to evaporate in a controlled manner over a longer period of time than those which do not possess a mono($C_1$ to $C_4$ alkyl) ether of diethylene glycol. It is to be understood that these examples are not intended to limit the generally broad scope of the present invention in strict accordance therewith.

EXAMPLE I

In this example a solid perfumed block was prepared by dissolving 8.5 grams of stearic acid in 54.0 grams of the monoethyl ether of diethylene glycol, said admixture being accomplished while maintaining the temperature of said mixture in a range of from about 70° to about 80° C. In like manner, 1.2 grams of anhydrous sodium hydroxide was dissolved in 4 grams of distilled water and 12.3 grams of ethylene glycol was added thereto, the temperature of this solution being also maintained in a range of from 70° to 80° C. After the sodium hydroxide was dissolved in one solution and the stearic acid was dissolved in the other solution, the two solutions were then thoroughly admixed for a period of 10 to 20 seconds. At the end of this time, 20 grams of a perfumery composite was added, the resulting solution being thoroughly admixed and placed into a mold. The mold was allowed to return to room temperature whereupon the mixture solidified and was then removed.

EXAMPLE II

In this example, a second solid block was prepared in a manner similar to that set forth in Example I above. However, the ethylene glycol was omitted from the formulation. The block was prepared by dissolving 8.5 grams of stearic acid in 76.3 grams of the monoethyl ether of diethylene glycol, the stearic acid being dissolved at a temperature of about 80° C. In like manner, 1.2 grams of sodium hydroxide was dissolved in 4 grams of distilled water at a temperature of 80° C. and the two solutions were then thoroughly admixed for a period of 10 to 20 seconds. Following this, 10 grams of a perfumery composite was then added, the resulting solution was admixed for an additional period of 10 to 20 seconds and the resulting solution was charged to a mold. The mold was allowed to cool to room temperature where the solution solidified to form a solid perfumed composition of matter of the present invention.

EXAMPLE III

In this example 8.5 grams of stearic acid is dissolved in 60 grams of the monomethyl ether of diethylene glycol, said dissolution being accomplished at a temperature of 80° C. In like manner, 1.2 grams of sodium hydroxide is dissolved in 4 grams of distilled water at a temperature of 80° C. following which 12.3 grams of propylene glycol is added to the alkali solution. The alkali solution of inert liquids and the stearic acid dissolved in the monomethyl ether of diethylene glycol are admixed with constant agitation during a period of 10 to 20 seconds. At the end of this time, a perfumery composite in the amount of 14 grams is added to the solution which is thereafter again admixed with constant agitation and poured into a mold. The mold and contents thereof are allowed to cool to room temperature and the resulting solid perfumed composition of matter is recovered from the mold.

EXAMPLE IV

In this example 8.5 grams of stearic acid is dissolved in 64 grams of the monopropyl ether of diethylene glycol at a temperature of 80° C. In a second reaction vessel, 1.2 grams of anhydrous sodium hydroxide is dissolved in 4 grams of distilled water at a temperature of 80° C. and 12.3 grams of ethylene glycol is added to the solution. The alkali solution of inert liquids is then added to the solution of the monopropyl ether of diethylene glycol containing the dissolved stearic acid, the addition being accomplished at a temperature of 80° C. After thoroughly admixing the two portions 10 grams of a perfumery composite is added and the resulting solution is poured into a mold. Upon cooling to room temperature, the resulting solid perfumed composition of matter is removed therefrom.

EXAMPLE V

To illustrate the ability of the solid perfumed compositions of matter of the present invention to evaporate at a more controlled rate for a longer period of time, a comparison was made in which a block prepared according to Example I above and which contained 10% of a perfume known in the trade as Fichtennadel was allowed to evaporate at room temperature. The starting block weighed 49 grams. The evaporation of the block is charted in Table I below:

TABLE I

| Weight in Grams | Days |
| --- | --- |
| 43 | 10 |
| 39 | 20 |
| 34 | 30 |
| 31 | 40 |
| 28 | 50 |
| 24 | 60 |
| 22 | 70 |
| 19.5 | 80 |
| 18 | 90 |

In contradistinction to this, an air freshener block sold by a major European company also was allowed to evaporate at room temperature. The results of this evaporation are set forth in Table II below. The initial weight of this block was 73 grams.

TABLE II

| Weight in Grams | Days |
| --- | --- |
| 38 | 10 |
| 30 | 20 |
| 26 | 30 |
| 24 | 40 |
| 21 | 50 |
| 19 | 60 |
| 18 | 70 |

It is therefore readily apparent from a comparison of the above two tables that the solid block which contained a mono($C_1$ to $C_4$ alkyl) ether of diethylene glycol, namely, the monoethyl ether of diethylene glycol, exhibited an evaporation rate which was more controlled and regular and, in addition, lasted for a longer period of time. For example, a comparison of the two blocks after a 10-day period of evaporation showed that over one-half of the total weight of the block which did not contain the monoethyl ether of diethylene glycol was lost by evaporation in contrast to the rate of evaporation of the block of the present invention which showed only a 10% loss of weight by evaporation during the first 10 days. At the 20-day period, it is to be noted that the block of the present invention only exhibited a 25% loss in weight by evaporation as contrasted to the block which did not contain all of the ingredients necessary for the controlled evaporation, the latter block exhibiting an over 50% loss in weight. To carry out the comparison for a longer period of time, it is to be noted that at 90 days, the block prepared according to the process of the present invention still maintained a weight approximately 36% of the original weight of the block as contrasted to the block which is in commercial use which possessed only 22% of its original weight after a period of 70 days.

It is therefore readily apparent from the above comparison that by utilizing a mono($C_1$ to $C_4$ alkyl) ether of diethylene glycol as one component in the formulation of a solid composition of matter, it is possible to form said composition of matter so that the evaporation with concurrent loss of the pleasant fragrance will be controlled and will permit the block to be used for a relatively longer period of time than is possible when utilizing solid perfumed compositions of matter which do not contain all of the components of the present invention.

I claim as my invention:

1. A solid perfumed composition of matter comprising a mixture of a gelling agent, inert liquids, an aromatic composite and a mono($C_1$ to $C_4$ alkyl) ether of diethylene glycol, said aromatic composite and said ether being of similar volatility and said ether being present in the solid composition in greater amount than said aromatic composite.

2. The composition of matter as set forth in claim 1 in which said gelling agent is present in an amount of from about 2% to about 10% by weight, said aromatic composite is present in an amount of from about 2% to about 20% by weight, said inert liquids are present in an amount of from about 10% to about 20% by weight and said mono($C_1$ to $C_4$ alkyl) ether of diethylene glycol is present in an amount of from about 45% to about 86% by weight of the solid composition of matter.

3. The composition of matter as set forth in claim 1 in which said mono($C_1$ to $C_4$ alkyl) ether of diethylene glycol is the monomethyl ether of diethylene glycol.

4. The composition of matter as set forth in claim 1 in which said mono($C_1$ to $C_4$ alkyl) ether of diethylene glycol is the monoether ether of diethylene glycol.

5. The composition of matter as set forth in claim 1 in which said mono($C_1$ to $C_4$ alkyl) ether of diethylene glycol is the monopropyl ether of diethylene glycol.

6. The composition of matter as set forth in claim 1 in which said gelling agent is the sodium salt of stearic acid.

7. The composition of matter as set forth in claim 1 in which said inert liquid is water.

8. The composition of matter as set forth in claim 1 in which said inert liquids comprise a mixture of water and ethylene glycol.

9. The composition of matter as set forth in claim 1 in which said inert liquids comprise a mixture of water and propylene glycol.

* * * * *